(12) United States Patent
Fukuma et al.

(10) Patent No.: US 6,844,925 B2
(45) Date of Patent: Jan. 18, 2005

(54) APPARATUS FOR MEASURING REFRACTIVE POWER

(75) Inventors: Yasufumi Fukuma, Tokyo (JP); Eiichi Yanagi, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 293 days.

(21) Appl. No.: 10/110,333

(22) PCT Filed: Aug. 13, 2001

(86) PCT No.: PCT/JP01/06983
§ 371 (c)(1),
(2), (4) Date: Apr. 10, 2002

(87) PCT Pub. No.: WO02/14827
PCT Pub. Date: Feb. 21, 2002

(65) Prior Publication Data
US 2002/0154292 A1 Oct. 24, 2002

(30) Foreign Application Priority Data
Aug. 11, 2000 (JP) ........................... 2000-244512

(51) Int. Cl.[7] ................................................ G01B 9/00
(52) U.S. Cl. ...................................... 356/127; 356/124
(58) Field of Search ................................ 356/124–127

(56) References Cited

U.S. PATENT DOCUMENTS 3,870,415 A  3/1975  Cornsweet
4,395,120 A  7/1983  Takahashi
4,796,991 A * 1/1989  Gordon et al. ............... 356/125
5,144,346 A  9/1992  Nakamura et al.
5,767,940 A  6/1998  Hayashi et al.
5,886,780 A  3/1999  Fukuma et al.

FOREIGN PATENT DOCUMENTS

| JP | 63-53433 | 3/1988 | .......... G01M/11/02 |
| JP | 4-9135 | 1/1992 | .......... A61B/3/103 |
| JP | 6-40834 | 5/1994 | .......... G01M/11/02 |
| JP | 10-14876 | 1/1998 | .......... A61B/3/10 |
| JP | 11-160201 | 6/1999 | .......... G01M/11/02 |

* cited by examiner

Primary Examiner—Gregory Toatley, Jr.
Assistant Examiner—Amanda Merlino
(74) Attorney, Agent, or Firm—Chapman and Cutler LLP

(57) ABSTRACT

A refracting power measuring apparatus according to the present invention comprises an optical system 1 for projecting a measuring light P toward a lens TL wet with liquid 12, a light receiving sensor 7 for receiving and outputting the measuring light P which passes through the lens TL, an arithmetic circuit 13 for calculating optical characteristic values based on a receiving signal, a residual quantity arithmetic circuit 14 for outputting a residual quantity signal based on characteristic value data of the arithmetic circuit 13, a delay circuit 19 for delaying the residual quantity signal, a comparing circuit 18 which compares a residual quantity signal delayed by the delaying circuit 19 and the following residual quantity signal and judges whether a difference therebetween is less than an allowed value.

18 Claims, 9 Drawing Sheets

APPARATUS FOR MEASURING REFRACTIVE POWER

TECHNICAL FIELD

The present invention relates to a refracting power measuring apparatus (lens meter, an eye-refracting power measuring apparatus) which is capable of measuring precisely optical characteristic values of a soft contact lens in air.

BACKGROUND ART

Hitherto, a soft contact lens is softer rather than a hard contact lens and therefore the configuration of the soft contact lens is easy to deform under its own gravity in measuring optical characteristics while holding the soft contact lens in a lens receiver in air. When the soft contact lens includes a large quantity of water, the water in the soft contact lens evaporates while the soft contact lens is held in air a long time.

Accordingly, an error is easy to occur in measurement of the optical characteristic values for the soft contact lens in air and essence and quickness are required to measure the soft contact lens in air. A lens meter (refracting power measuring apparatus) is being developed to measure the optical characteristic values with holding a configuration of the soft contact lens which is dipped in water.

In the meter, because the optical characteristic values can be measured with holding the configuration of the soft contact lens and without evaporating water, the essence is not required. The optical characteristic values of the soft contact lens can, also, be measured without the quickness being required.

However, the optical characteristic values of the soft contact lens measured in liquid are different from that measured in air.

In optical characteristic values measured in liquid, a difference between refractive indexes of the soft contact lens and liquid is less than a difference between refractive indexes of the soft contact lens and air.

Accordingly, the optical characteristic values of the soft contact lens measured in liquid are less than that measured in air. As a result, the optical characteristics of the soft contact lens in liquid must be converted into that measured in air. A refractive index of material of the soft contact lens is required to this conversion.

However, the refractive index of material of the soft contact lens is almost unknown in general. Thus, it is not able to correctly convert the optical characteristic values measured in liquid into the optical characteristic values in air which represent optical characteristic values of a soft contact lens which is worn in eye. As a result, there is a problem in which reliability of the converted optical characteristic values obtained by converting the optical characteristic values measured in liquid is lack.

It is an object of the present invention to provide a refracting power measuring apparatus in which optical characteristic values of a soft contact lens can be precisely measured in air.

DISCLOSURE OF INVENTION

A refracting power measuring apparatus recited in claim 1 comprises a measuring optical system for projecting a measuring light toward a soft contact lens wet with liquid to measure optical characteristic values of the soft contact lens in air, a light receiving optical system having a light receiving sensor which receives the measuring light passed through the soft contact lens and outputs a received signal, an arithmetic circuit in which the received signal is inputted and computes the optical characteristic values based on the received signal, a residual quantity arithmetic circuit in which optical characteristic values data corresponding to the optical characteristic values of the arithmetic circuit are inputted every sample time and computes a residual quantity by means of a statistical processing based on the optical characteristic values data to output the residual quantity signal, a delay circuit for delaying the residual quantity signal by a time corresponding to the sample time, a comparing circuit for comparing the residual quantity signal delayed by the delay circuit with the following residual quantity signal and judging whether a difference between the delayed and following residual quantity signals is less than an allowed values. The apparatus is characterized in that the optical characteristic values in air can be obtained based on judged results of the comparing circuit.

A refracting power measuring apparatus recited in claim 2 is characterized in that a setting switch is provided which establishes a measuring mode to measure the optical characteristic values of the soft contact lens in air.

A refracting power measuring apparatus recited in claim 3 is characterized in that the residual quantity is computed by receiving at least three beams or more as measuring beams.

A refracting power measuring apparatus recited in claim 4 is characterized in that it comprises a measuring optical system for projecting a measuring light toward the soft contact lens wet with liquid to measure the optical characteristic values of the soft contact lens in air, a light receiving optical system having a light receiving sensor which receives the measuring light passed through the soft contact lens and outputs a received signal, an arithmetic circuit in which the received signal is inputted and computes the optical characteristic values based on the received signal, a residual quantity arithmetic circuit in which optical characteristic values data corresponding to the optical characteristic values of the arithmetic circuit are input every sample time and computes a residual quantity by means of a statistical processing based on the optical characteristic values data to output the residual quantity signal, a memory storing means to memorize the residual quantity computed by the residual quantity arithmetic circuit, a judging means to judge whether a difference is a predetermined values with computing the difference in sequence of time based on the residual quantity stored in the memory storing means, a display means to represent with extracting optical characteristic values corresponding to a difference which is less than a predetermined values.

A refracting power measuring apparatus recited in claim 5 is characterized in that the measuring optical system is a pattern beam projecting optical system which projects a ring shaped pattern beam for measuring a refracting power of the soft contact lens on a reflected surface (eye ground of a model eye) through the soft contact lens, the light receiving optical system guides the ring shaped pattern beam which is reflected on the reflected surface and returned through the soft contact lens to the light receiving element, a portion of an optical system of the pattern beam projecting and light receiving optical systems is shared, and provided in the shared portion of the pattern beam projecting and light receiving optical systems is a deflecting member which deflects and projects the ring shaped pattern beam with respect to an optical axis of the pattern beam projecting optical systems.

A refracting power measuring apparatus recited in claim 6 is characterized in that the deflecting member is a deflecting prism which is rotated about the optical axis of the pattern beam projecting optical system.

A refracting power measuring apparatus recited in claim 7 is characterized in that the reflected surface is disposed in a conjugate position with eye ground of a tested eye and a refracting power of the tested eye can be measured by use of the pattern beam projecting and light receiving optical systems in removed condition of a model eye.

A refracting power measuring apparatus recited in claim 8 is characterized in that the deflecting member is inserted into a position which is not conjugate with a disposed position of the soft contact lens in measuring the optical characteristic values of the soft contact lens.

A refracting power measuring apparatus recited in claim 9 is characterized in that it comprises a measuring optical system for projecting a measured bean toward a soft contact lens to measure optical characteristic values of the soft contact lens in air, a light receiving optical system having a light receiving sensor which receives a measuring light passed through the soft contact lens and outputs a light receiving signal, an arithmetic optical system in which the light receiving signal is input and computes the optical characteristic values based on the light receiving signal, the measuring optical system is a pattern beam projecting optical system which projects a pattern beam for measuring a refracting power of the soft contact lens on a reflected surface through the soft contact lens, the light receiving optical system guides the pattern beam which is reflected on the reflected surface and returned through the soft contact lens to the light receiving element, a portion of an optical system of the pattern beam projecting and light receiving optical systems is shared, and provided in the shared portion of the pattern beam projecting and light receiving optical systems is a deflecting member which deflects and projects the ring shaped pattern beam with respect to an optical axis of the pattern beam projecting optical systems and the deflecting member is a deflecting prism which is rotated about an optical axis.

A refracting power measuring apparatus recited in claim 10 is characterized in that the deflecting prism is inserted into a position which is not conjugate with a disposed position of the soft contact lens to cause the pattern beam to oscillate on the soft contact lens in measuring the optical characteristic values of the soft contact lens.

BRIEF DESCRIPTION OF DRAWINGS

FIG. 2 is an enlarged view showing a change of a surface state of a soft contact lens according to the present invention wherein FIG. 2(a) is a view showing a state of a soft contact lens wet by a large quantity of water, FIG. 2(b) is a view showing a soft contact lens with a smooth surface wet by a suitable quantity of liquid, and FIG. 2(c) is a view showing a dry soft contact lens with a rough surface.

FIG. 4 is a explanatory view a pattern image formed on a light receiving sensor by means of a pattern plate shown in FIG. 2 wherein FIG. 4(a) is a view showing a relationship between a soft contact lens and a pattern, FIG. 4(b) is a view showing an example of the pattern image formed on the light receiving sensor, and FIG. 4(c) is a view showing an approximate elliptical pattern image formed by the light receiving sensor, in a S-curve developed state.

BEST MODE FOR CARRYING OUT THE INVENTION

Embodiment 1

Figure 1:
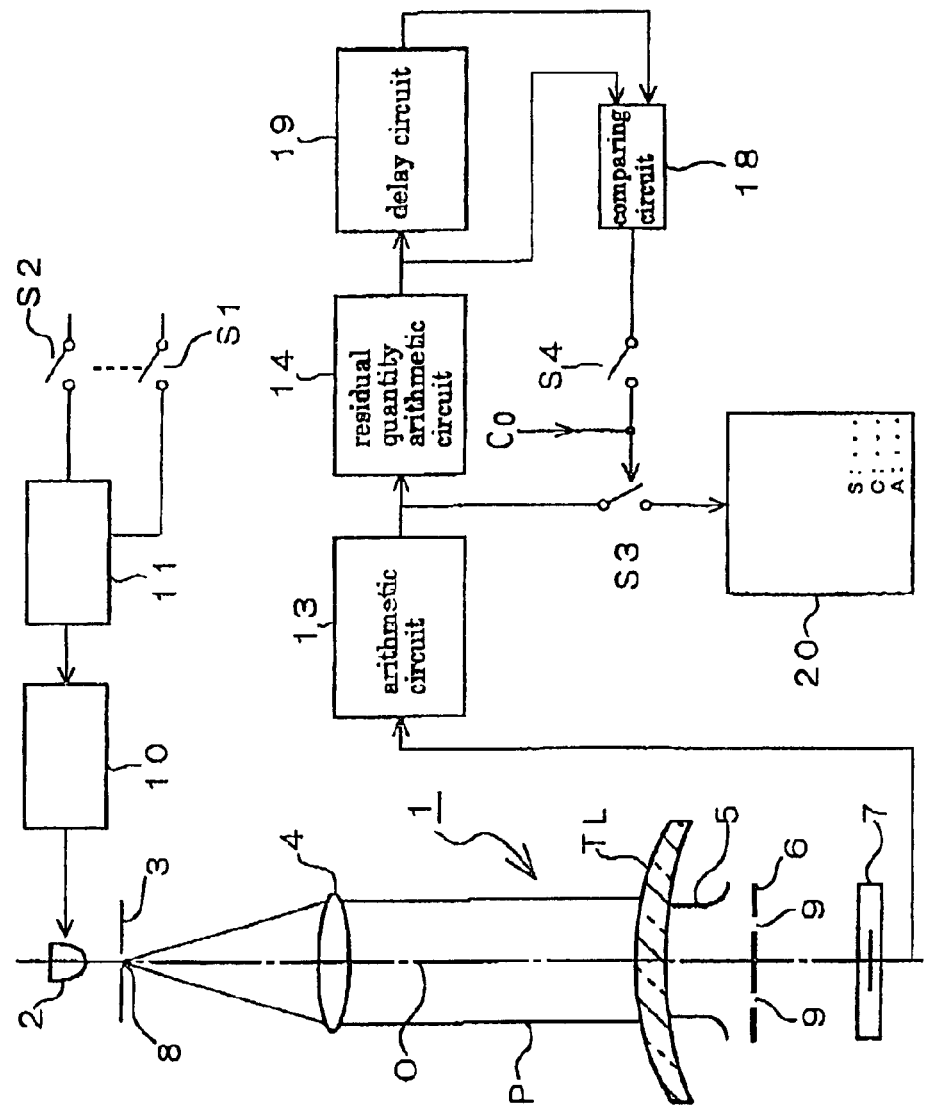
FIG. 1 is a block view of an optical system of a lens meter as a refracting power measuring apparatus and a processing circuit thereof according to a first embodiment of the present invention.

In FIG. 1, reference numeral 1 denotes a measuring optical system of a lens meter as a refracting power measuring apparatus. The measuring optical system 1 comprises a measuring light source 2, a pin hole plate 3, a collimate lens 4, a lens receiving cylinder 5, a pattern plate 6, and a light receiving sensor 7 of a CCD and so on. Note that reference numeral O denotes a light axis.

The measuring light source 2 is emitted light by means of a drive circuit 10 which is turned on by switches S1 and S2 of an operating control circuit 11.

The switch S1 functions to establish the lend meter in a mode which measures an optical characteristic values of a soft contact lens TL in air.

The switch S2 functions to establish the lens meter in measuring modes of examined lenses other than a soft contact lens meter, for example, a hard contact lens and lenses in eye glasses.

Figure 2:
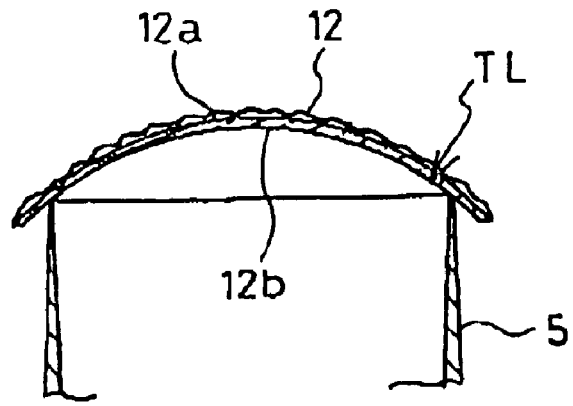
Figure 2:
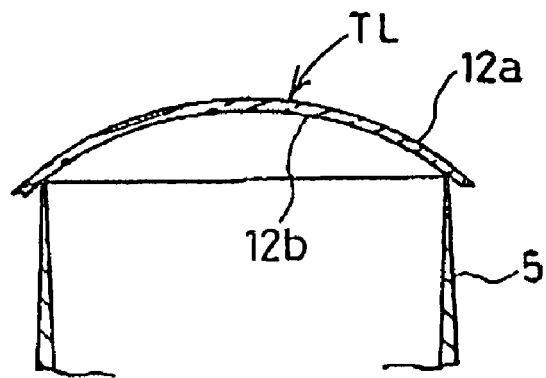
Figure 2:
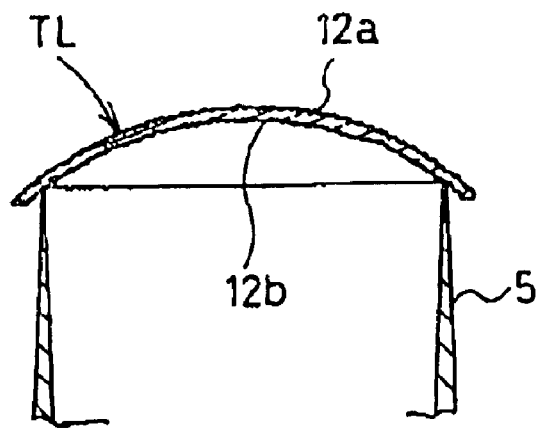

A measuring light is passed through a pin hole in the pin hole plate and is projected toward the lens receiving cylinder 5 as a parallel measuring light P by the collimate lens 4. The soft contact lens TL is disposed on the lens receiving cylinder 5. The soft contact lens is dipped in physiological saline solution or adapted to drop the physiological saline solution by a spuit (not shown) and therefore a large quantity of physiological saline solution or water (liquid 12) is stuck to the soft contact lens when measuring is started as shown in FIG. 2.

Figure 3:
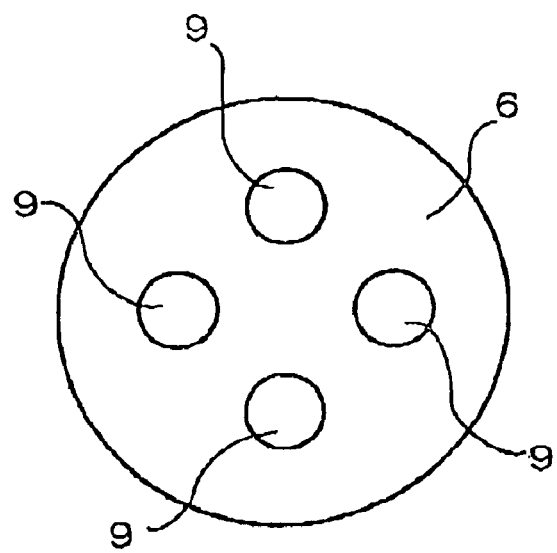
FIG. 3 is a plan view of a pattern plate shown in FIG. 1.

The parallel measuring light P is subjected to refract in passing through the soft contact lens TL and guided to the pattern plate 6. The pattern plate 6 is provided with four opening patterns 9 as shown in FIG. 3 and a pattern image by the measuring light passed through the opening patterns (as described hereinafter) is formed in the light receiving sensor 7. The light receiving sensor is used with, for example, a two dimensional area CCD.

When the soft contact lens TL is not set on the lens receiving cylinder 5, the same pattern images as the opening patterns 9 are projected on the light receiving sensor 7. When the soft contact lens TL is a concave lens, an enlarged pattern image is projected on the light receiving sensor 7. When the soft contact lens TL is a convex lens, a reduced pattern image is projected on the light receiving sensor 7. A light receiving output of the light receiving sensor 7 is inputted into a SCA arithmetic circuit 13 which computes the optical characteristic values, The SCA arithmetic circuit 13 computes a spherical degree S, a refracting degree C, and an axis angle A as optical characteristic values of the soft contact lens TL. The SCA arithmetic circuit 13 outputs the data of the optical characteristic values to a residual quantity arithmetic circuit 14. which computes the residual quantity with a known statistical practice.

The soft contact lens TL is wet with liquid to attach a large quantity of liquid 12 as shown in FIG. 2(a). If the soft contact lens TL suitably dries and absorption of the liquid by the soft contact lens proceeds during measuring, the liquid 12 is adapted to a front surface 12a of the soft contact lens TL to make the front surface 12a and a back surface 12b of the soft contact lens smooth as shown in FIG. 2(b). Furthermore, if the soft contact lens TL dries during measuring, the front and back surfaces 12a, 12b of the soft contact lens TL become rough as shown in FIG. 2(c).

Because a configuration of the front and back surfaces 12a, 12b is complicated when the soft contact lens TL is wet with liquid to attach a large quantity of liquid as shown in FIG. 2(a), the parallel measuring light P is subjected to a deformation corresponding to the configuration. Accordingly, the optical characteristic values S, C, A of the soft contact lens TL are different from the inherent optical characteristic values S, C, A of the soft contact lens TL in air. Also, the parallel measuring light P has a characteristic that when the liquid 12 is adopted to the front surface 12a of the soft contact lens TL, these optical characteristic values S, C, A are strictly the same as the inherent optical characteristic values S, C, A of the soft contact lens in air. Furthermore, when the font and back surfaces 12a, 12b of the soft contact lens TL is rough as shown in FIG. 2(c), the parallel measuring light P is subjected to a deformation corresponding to a roughness of the front and back surfaces 12a and 12b. Consequently, the optical characteristic values S, C, A of the soft contact lens are different from the optical characteristic values S, C, A in air resulting from an inherent configuration of the soft contact lens TL. When astigmatism component is included in the soft contact lens TL, the pattern image (optical point image) of the parallel measuring light P which is passed through the soft contact lens TL and the opening patterns 9 of the pattern plate 6 as shown in FIG. 4(a) ideally exists on a line of virtual ellipse 15 as shown in FIG. 4(b).

Figure 4:
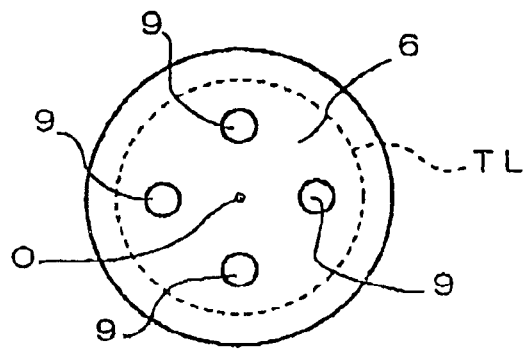
Figure 4:
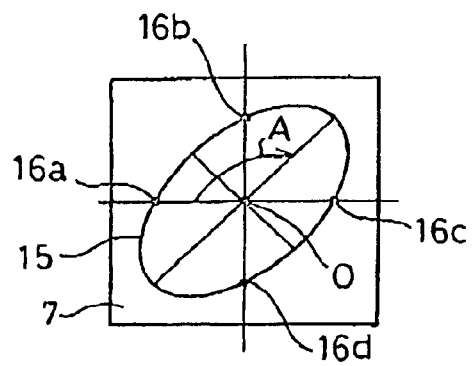
Figure 4:
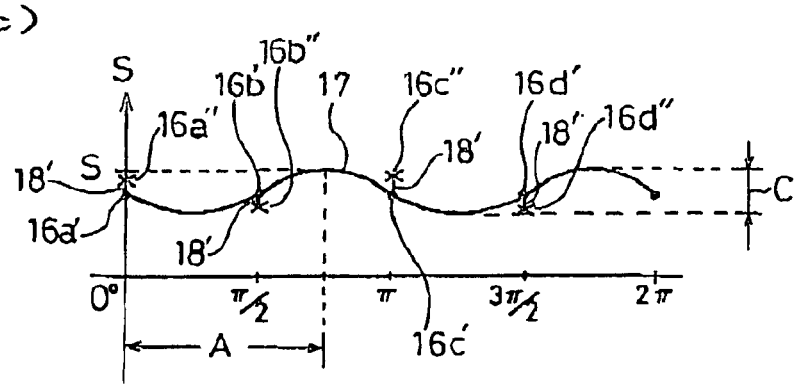

In FIG. 4(b), reference numerals 16a~16d denote pattern images which the light receiving sensor 7 receives thereon. When a large quantity of liquid attach to the front and back surfaces 12a and 12b of the soft contact lens TL as shown in FIG. 2(a), the pattern images 16a~16d greatly deflect from the line of the virtual ellipse 15. When the front and back surfaces 12a and 12b of the soft contact lens TL are rough as shown in FIG. 2(c), the pattern images 16a~16d, also, deflect from the line of the virtual ellipse. A developed curve 17 of spherical degree S which is figured based on FIG. 4(b) is shown in FIG. 4(c).

Positions 16a'~16d' of the pattern images (optical point images) 16a~16d ideally exist on the line of the developed curve 17 of the spherical degree S. However, the soft contact lens TL is practically measured, the pattern images 16a~16d deflect from the developed curve 17 as shown at the positions 16a"~16d".

In other words, in the statistical practice, a sine curve 17 is obtained by least square-method based on the positions 16a"~16d" of the pattern images 16a~16d obtained, the residual 18' from the developed curve is computed and the sum (residual quantity) of the residual 18' is obtained. This residual 18' may be obtained about all the optical characteristic values S, C, A or any one thereof. The residual 18' may, also, be obtained based on the positions 16a'~16d' on the light receiving sensor 7 of the pattern images 16a~16d.

Here, the residual quantity arithmetic circuit 14 calculates the residual based on the spherical degree S. The residual is calculated at every a sampling time $\Delta t$ (for example, 0.01 second) and the data of the sum (residual quantity) are inputted in a comparing circuit 18 and a delaying circuit 19. The delaying circuit 19 delays the data of the sum by a time corresponding to the sampling time $\Delta t$ to output toward the comparing circuit 18. The comparing circuit 18 compares a residual quantity signal delayed by the delay circuit 19 and the following residual quantity signal and judges whether a difference between these signals is less than a predetermined value. The comparing circuit 18 functions switching-on a switch S3 through a switch S4. The switch S4 is switched-on in cooperation with a switch S1.

Figure 5:
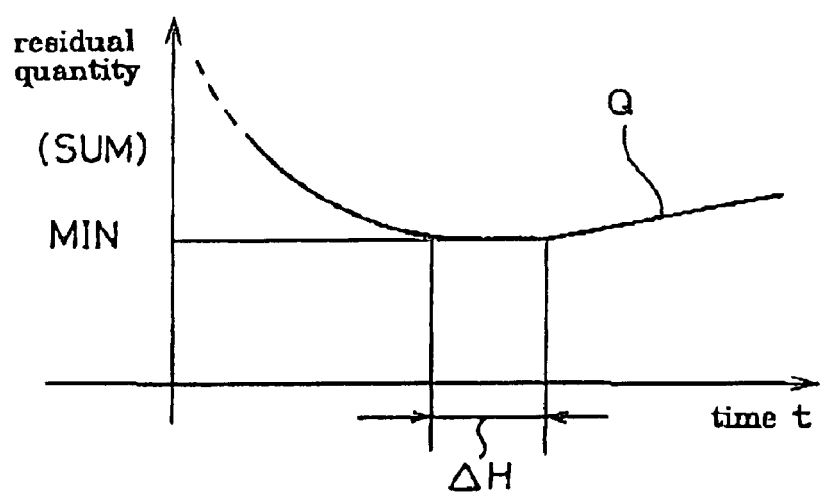
FIG. 5 is an explanatory view of a residual curve.

As shown in FIG. 5, the residual quantity SUM reduces gradually when time t lapses from the start of the measurement and again increases with getting a minimum value MIN as shown in a residual curve Q. A areas $\Delta H$ of the minimum value MIN of the residual curve Q corresponds to the state as shown in FIG. 2.

Namely, the comparing circuit 18 calculates a difference between the residual quantity SUM before one and the residual quantity SUM after one and judges whether the difference $\Delta SUM$ of the residual quantity is about similar to zero. When the difference $\Delta SUM$ is about similar to zero, the switch S3 is switched-on to cause calculated results of the spherical degree S, cylindrical degree C, and axial angle A to represent on a monitor 20. As needed, the calculated results of the spherical degree S, cylindrical degree C, and axial angle A may be stored in a memory storing means such as a floppy disk, a hard disk.

According to the mode for carrying out the invention, optical characteristic values can be automatically measured with adapted the front and back surfaces 12a, 12b of the soft contact lens TL to the liquid 12 as shown in FIG. 2(a) without requiring the essence and experience of the examiner. Consequently, the optical characteristic values of the soft contact lens can be precisely measured in air.

Note that when a tested lens other than soft contact lens TL is measured, as the switch S2 is switched-on, the switch S3 is switched-on by a control signal CO and simultaneously with the measurement, the calculated results of the spherical degree S, cylindrical degree C, axial angle A are displayed on the monitor 20.

In the mode described above, there is provided a configuration in which the residual quantity of one before and the residual of one after are calculated by use of the delayed circuit 19. In the stead of adopting this configuration, the delayed circuit 19 is not required by providing memory storing means for memorizing and storing optical characteristic values at every the sample time and residual quantity arithmetic means for calculating a difference of residual quantities in time sequence based on the optical characteristic values stored in the memory storing means.

Namely, it is, also, able to provide memory storing means for memorizing the calculated result by the residual quantity arithmetic circuit 14, judging means which calculates the difference in time sequence based on the residual quantity stored in the memory storing means and judges whether the difference is a predetermined value. Optical characteristic values corresponding to the difference which is less than a predetermined value are extracted and displayed on the monitor 20 as display means.

In the mode mentioned above, the pattern images are obtained by use of the pattern plate 6 and the residual quantity is obtained by calculating the S, C, and A from the pattern images. However, Aberration is obtained by use of a wave surface sensor (see a lens meter and a positive optical reflecting telescope in a Japanese Patent Application No. Hei 11-375223: filed on December 28, Hei 11), and the residual quantity may be calculated from the aberration.

Embodiment 2

Figure 6:
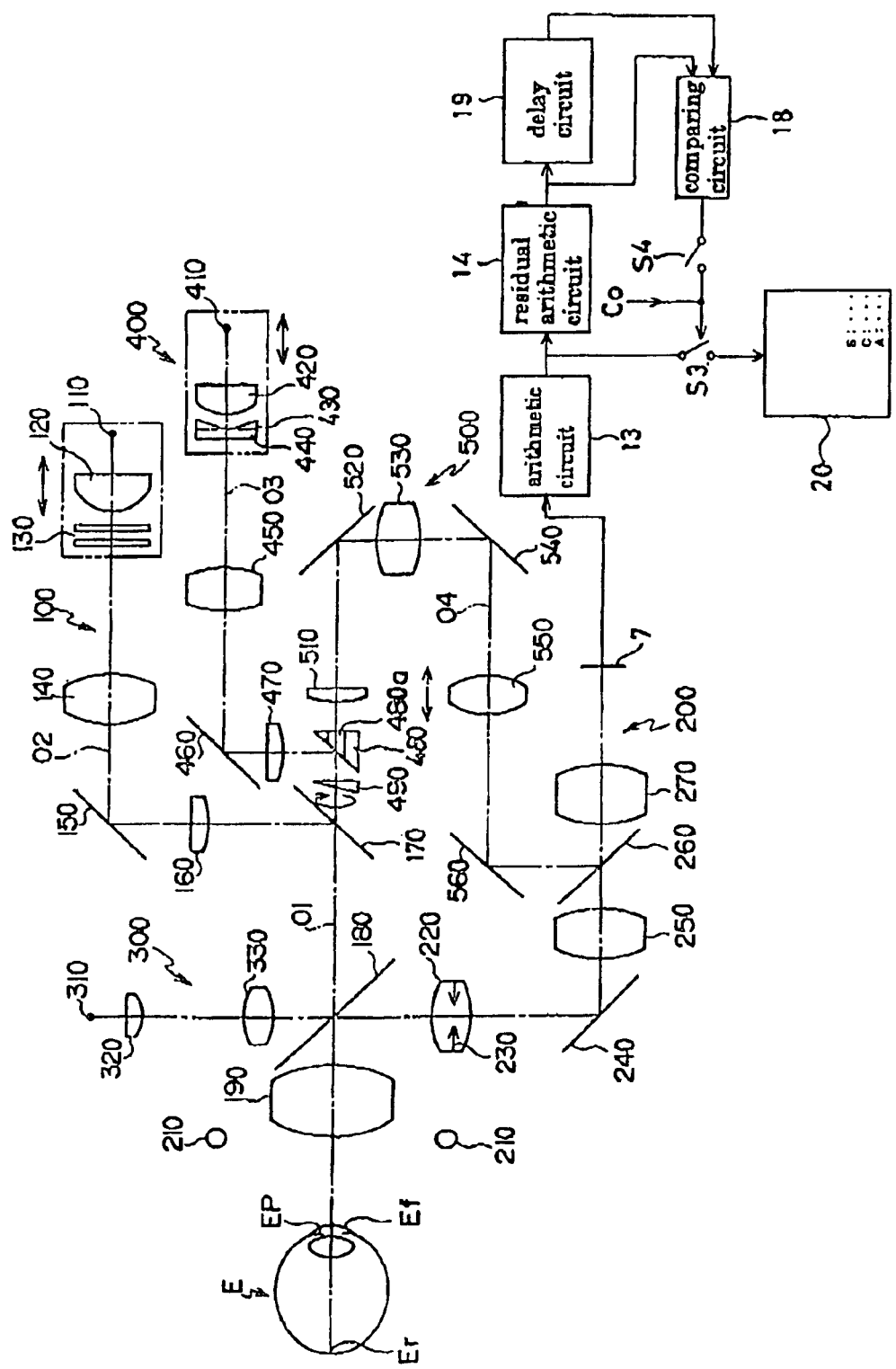
FIG. 6 is an explanatory view of an optical system of a refracting power measuring apparatus according to a second embodiment of the present invention.

FIG. 6 is an explanatory view of an optical system applied the present invention to a refracting power measuring apparatus.

In FIG. 6, numeral 100 is a viewing target projecting optical system for projecting a view target for performing fixed sight-foggy sight of an examined eye E to the eye ground Er, numeral 200 is a monitoring optical system for monitoring a front eye portion Ef of the examined eye E, numeral 300 is a scale projecting optical system for projecting a sighting scale to the light receiving sensor 7, numeral 400 is a ring shaped pattern beam projecting optical system for projecting a ring shaped pattern beam which measures a refracting power of the examined eye E to the eye ground Er, numeral 600 is a light receiving optical system for causing the beam reflected on the eye ground Er to receive on the light receiving sensor 7.

The view target projecting optical system 100 comprises a light source 110, a collimator lens 120, a view target plate 130, a relay lens 140, a mirror 150, a relay lens 160, a dichroic mirror 170, a dichroic mirror 180, and an objective 190.

After a visible light emitted from the light source 110 is formed into a parallel beam by the collimator lens 120, it passes through the view target plate 130. The view target plate 130 is provided with a target which performs the fixed-foggy sight of the examined eye E. The target beam is reflected on the mirror 150 with passing through the relay lens 140. The reflected beam reflected on the mirror 150 is reflected on the dichroic mirror 170 through the relay lens 160 to direct to a main optical axis O1 of an apparatus body. The reflected beam reflected on the dichroic mirror 170 passes through the dichroic mirror 180 and thereafter is guided to the examined eye E through the objective 190.

Note that the light source 110, collimator lens 120 and view target plate 130 are united and are movable along the optical axis O2 of the view target projecting optical system 100 to perform the fixed-foggy sight of the examined eye E. The monitoring optical system 200 includes a light source 210, an objective 190, a dichroic mirror 180, a relay lens 220, a diaphragm 230, a mirror 240, a relay lens 250, a dichroic mirror 260, a focus lens 270, and the light receiving sensor 7.

A beam emitted from the light source 210 illuminates directly the front eye portion Ef of the examined eye E. The beam reflected on the front eye portion Ef is reflected on the dichroic mirror 180 through the objective 190. The reflected beam reflected on the dichroic mirror 180 passes through the relay lens 220 and simultaneously passes trough the diaphragm 230 and then is reflected on the mirror 240. The reflected beam on the mirror 240 is passed through the relay lens 250 and dichroic mirror 260 and is focused on the light receiving sensor 7 by the focus lens 270.

The scale projecting optical system 300 includes a light source 310, a collimator lens 320 having a sighting scale, a relay lens 330, the dichroic mirror 180, the relay lens 220, the diaphragm 230, the mirror 240, the relay lens 250, the dichroic mirror 260, the focus lens 270, and the light receiving sensor 7.

A beam emitted from the light source 310 is formed into a sighting scale beam (parallel beam) as it passes through the collimator lens 320. The sighting scale beam is reflected on the mirror 240 through the relay lens 330, dichroic mirror 180, relay lens 220, and diaphragm 230. The sighting scale beam reflected on the mirror 240 is focused on the light receiving sensor 7 by the focus lens 270 through the relay lens 250 and dischroic mirror 260.

Displayed on the monitor 20 is a front eye portion image introduced by the monitoring optical system 200 and an image according to the sighting scale. The examiner performs operation of alignment in up, down, right and left directions of the examined eye E and the apparatus body to approach the front eye portion image displayed on the monitor 20 to the sighing scale image. The examiner, also, performs operation of forward and backward alignments. Note that when a refracting power is measured after the operation of alignment is terminated, the light sources 210 and 310 are turned off or a light to the light receiving snsor 7 is blocked by providing a shutter and so on in a light path extending from the dichroic mirror 260.

The ring-shaped pattern beam projecting optical system 400 comprises a light source 410, a collimator lens 420, a conical prism 430, a ring index plate 440, a relay lens 450, a mirror 460, a relay lens 470, a perforated prism 480, an optical axis deflecting prism 490 as a deflecting member, the dichroic mirror 170, the dichroic mirror 180 and the objective 190. Note that the light source 410 and the ring index plate 440 are optically conjugate. The ring index plate 440 and a pupil Ep of the examined eye E are also, disposed in an optically conjugate position.

A beam emitted from the light source 410 is formed into a parallel beam by the collimator lens 420 and is guided to the ring index plate 440 with passing through the conical prism 430. The ring index plate 440 is formed with a ring shaped pattern portion. The parallel beam passes through the ring shaped pattern portion to become a ring shaped pattern beam. The ring shaped pattern beam is passed through the relay lens 450 and thereafter is reflected on the mirror 460. The ring shaped pattern beam reflected on the mirror 460 is reflected in a direction along the main optical axis O1 by the perforated prism 480 with passing through the relay lens 470. The ring shaped pattern beam reflected on the perforated prism 480 is deflected in a diagonal direction deviated from the main optical axis O1 by the optical axis deflecting prism 490 and is guided to the dichroic mirrors 170, 180. The ring shaped pattern beam passed through the dichroic mirrors 170, 180 is focused on the eye ground Er by the objective 190.

Figure 7:
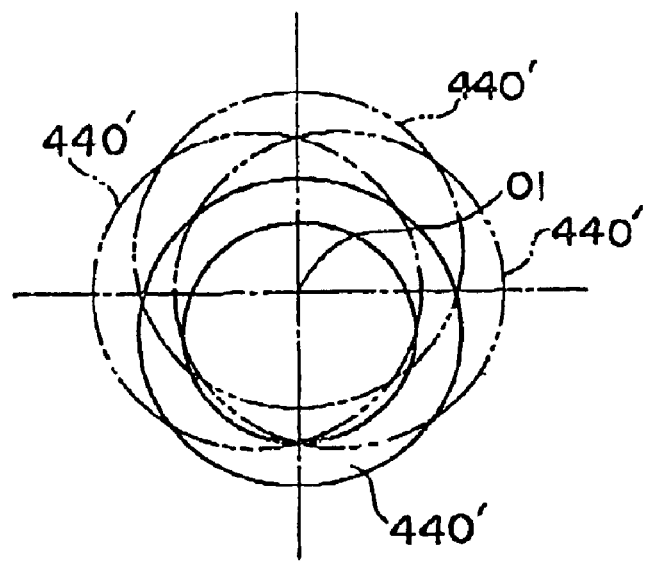
FIG. 7 is an explanatory view showing a state of a ring shaped pattern beam.

The optical axis deflecting prism 490 is rotated at a high speed (see arrow) about the main optical axis O1. The ring shaped pattern beam 440' projected on the eye ground Er by the high speed is rotated about the main optical axis O1 in the deflected state as shown in FIG. 7.

The light receiving optical system 500 comprises the objective 190, the dichroic mirrors 180 and 170, the optical axis deflecting prism 490, a perforated portion 480a of the perforated prism 480, a relay lens 510, a mirror 520, a relay lens 530, a mirror 540, a focused lens 550, a mirror 560, the dichroic mirror 260, the focus lens 270 and the light receiving sensor 7. Note that the focused lens 550 is movable along the axes O3 and O4 of each of the optical systems 400 and 500 together with the light source 410, collimator lens 420, conical prism 430 and ring index plate 440.

The ring shaped pattern beam guided to the eye ground Er by the pattern beam projecting optical system 400 is reflected on the eye ground Er to become an eye ground reflected beam. The eye ground reflected beam is collected on the objective 190. The eye ground reflected beam collected on the objective 190 is guided to the optical axis deflecting prism 490 with passing through the dichroic mirrors 180 and 170. The beam reflected on the eye ground is guided to the perforated portion 480a of the perforated prism 480 with passing through the optical axis deflecting prism 490. The eye ground reflected beam passes through the perforated portion 480a.

The eye ground reflected beam passed through the perforated portion 480a is guided to the mirror 620 through the relay lens 510. The eye ground reflected beam reflected on the mirror 520 is guided to the mirror 540 through the relay lens 530 and then is reflected on the mirror 540.

The eye ground reflected beam reflected on the mirror 540 is reflected on the mirror 560 and dichroic mirror 260 with passing through the focused lens 550 to focus the ring shaped pattern projecting image according to the eye ground reflected beam on the light receiving sensor 7 by the focusing lens 270. Upon termination of alignment of the apparatus body, the conjugate relationship of the light receiving sensor 7 and eye ground is held.

According to the configuration, each of the light sources 110, 210 and 310 is turned on, the examined eye is fixed sight and the alignment operation of the examined eye E and apparatus body is performed. When the alignment is complicated, the light sources 110, 210, 310 are turned off and the light source 410 is turned on.

Figure 8:
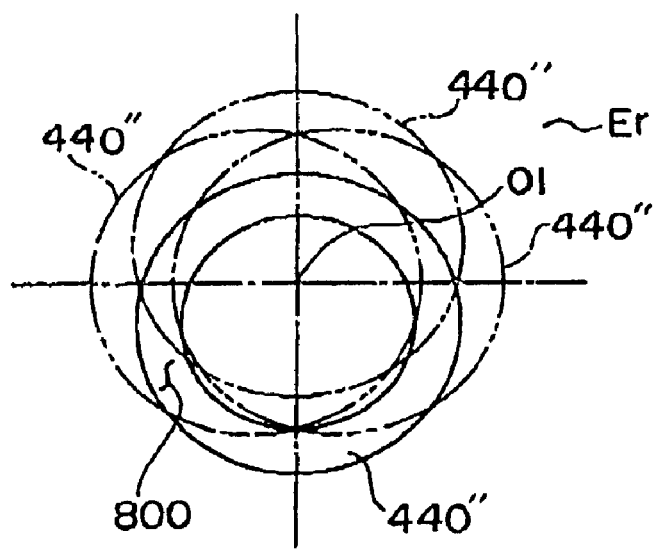
FIG. 8 is an explanatory view showing a state of a pattern image focused on eye ground.

An illuminated beam emitted from the light source 410 becomes the ring shaped pattern beam 440' by passing through the ring index plate 440 and is guided to the optical axis deflecting prism 490. The ring shaped pattern beam 440' passed through the optical axis deflecting prism 490 is projected on the eye ground Er and a ring shaped pattern image 440" is projected on the eye ground Er. FIG. 8 shows the ring shaped pattern image 440" projected on the eye ground Er.

Figure 9:
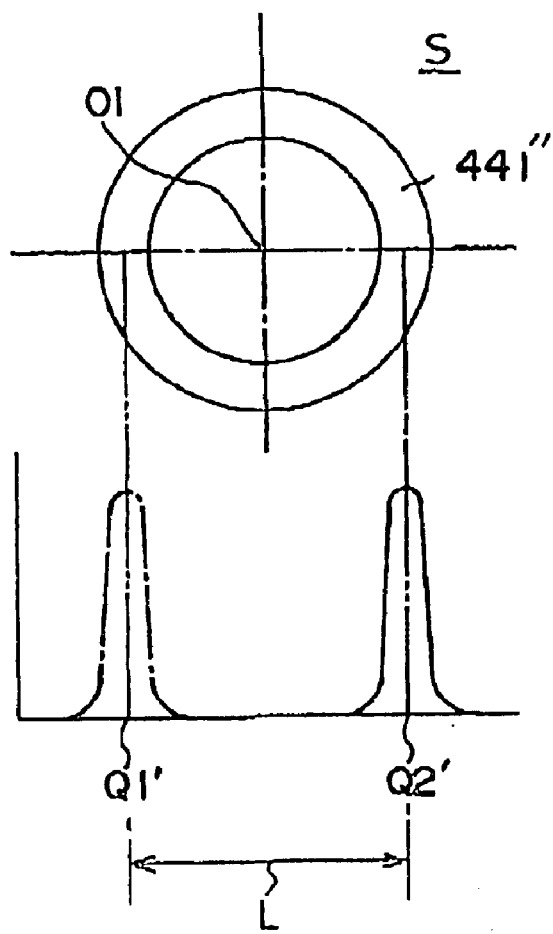
FIG. 9 is an explanatory view showing a ring shaped pattern projecting image formed on a light receiving sensor based on a ring shaped pattern beam reflected on the eye ground.

The reflected beam reflected on the eye ground Er is guided to the optical axis deflecting prism 490 and is focused on the light receiving sensor 7 as a pattern image 441" centered on the optical axis O1 again by the principle of beam reverse progress as shown in FIG. 9.

Operation of a measurement carrying-out switch by the examiner, causes some of the ring shaped pattern projecting image 441" on the light receiving element S based on the pattern image 440' which is focused at any position of rotation projected on the eye ground Er to memorize in a memory medium such as a frame memory.

In the refracting power measuring apparatus, when the examined eye is in normal vision (±0 diopter), the ring shaped pattern projecting image 441" having a ring shaped substantially complete round of a predetermined size of diameter is focused on the light receiving sensor 7. When the examined eye is in far slightness, the ring shaped pattern projecting image 441" having a diameter more than that of the normal vision is focused on the light receiving sensor 7. When the examined eye is in near slightness, the ring shaped pattern projecting image 441" having a diameter less than that of the normal vision is focused on the light receiving sensor 7. When the examined eye is in astigmatism, the ring shaped pattern projecting image becomes an elliptical shape.

Also, as shown in FIG. 9, detected are peal positions of center positions Q1', Q2' of image width in the ring shaped pattern projecting image 441" focused on the light receiving sensor 7. A refracting power and so on can be obtained by calculating a distance L between the centers Q1', Q2'of the ring shaped pattern projecting image 1' based on the detected peak positions Q1', Q2'. By use of the refracting power measuring apparatus, if there is disorder 800 in the eye ground Er as shown in FIG. 8, the refracting power can measured with reducing influence of the disorder (see Japanese Patent No. 3071693, Japanese Patent Application Hei-8-172716, Title of Invention: Refracting Power measuring Apparatus).

Figure 11:
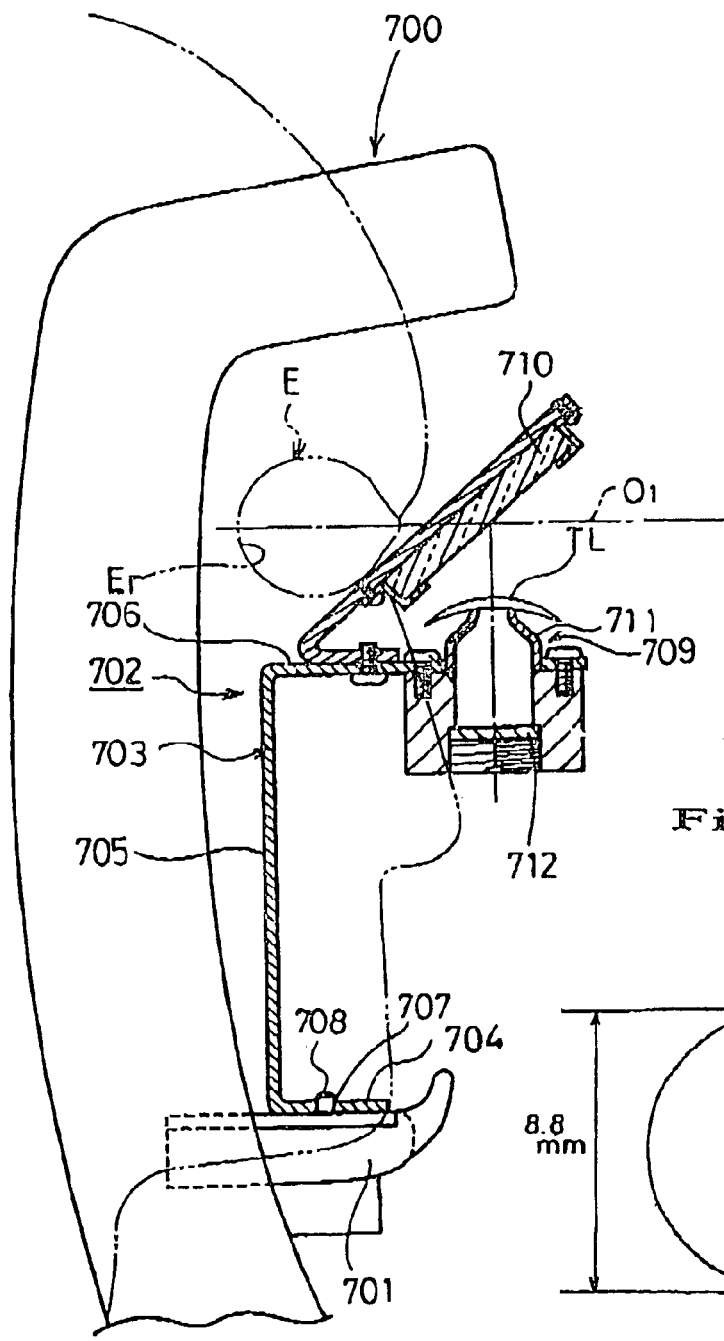
FIG. 11(a) is an explanatory view in measuring the soft contact lens by use of the eye-refracting power measuring apparatus showing in FIG. 6.
FIG. 11(b) is a view showing a rotated state of the ring shaped pattern beam on a surface of the soft contact lens.
Figure 11:
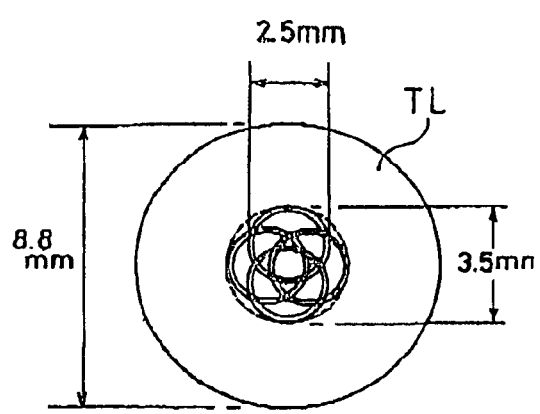
Figure 12:
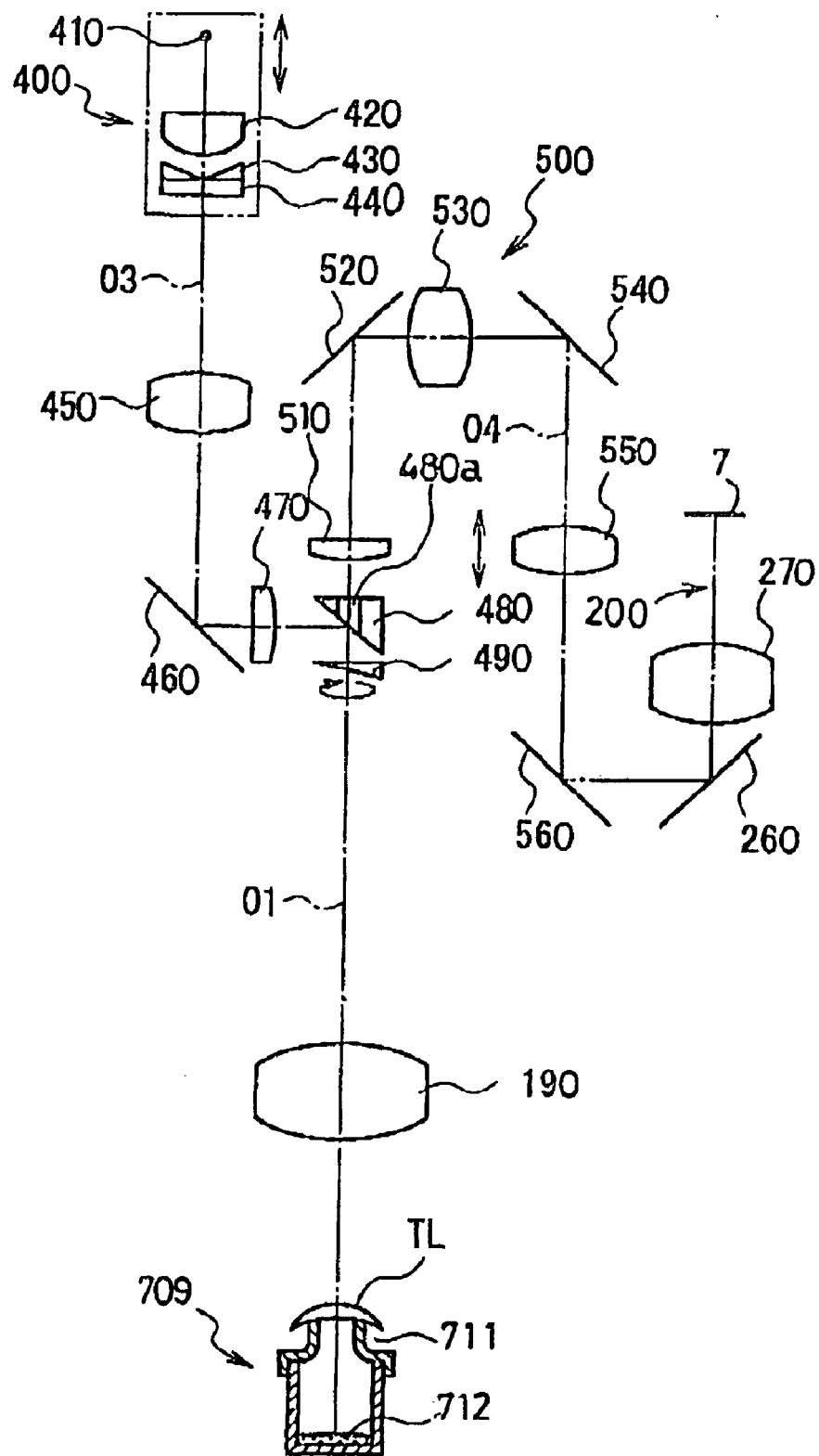
FIG. 12 is an explanatory view showing a modified example of an optical system of a refracting power measuring apparatus according to an embodiment 2 of the present invention.

When optical characteristics of a soft contact lens are measured, a model eye mounting device 702 is mounted on a chin receiver 701 of a chin receiving device 700 (see FIG. 11 (a)) constructing a portion of the refracting power measuring apparatus. The model eye mounting device 702 has a mounting plate 703. The mounting plate 703 comprises a pedestal plate portion 704, a standing plate portion 705 and a mounting plate portion 706. The pedestal plate portion 704 is provided with a pair of engaging holes 707. A pair of projecting pins 708 which are known and provided on the chin receiver 701 are inserted into the engaging holes 707. Consequently, the model eye mounting device 702 is movably mounted on the chin receiving device 701.

A model eye device 709 and a reflected mirror 710 are mounted on the mounting plate portion 706. The model eye device 709 comprises a lens receiver 711 and a reflected mirror 712 (reflected surface) which is provided in a conjugate position with the eye ground Er.

The ring shaped pattern beam is reflected on the reflected mirror 710 and guided to the reflected mirror 712 through the soft contact lens TL and then is reflected on the reflected mirror 712. The ring shaped pattern beam reflected on the reflected mirror 712 is again reflected on the reflected mirror 710 through the soft contact lens TL and is guided to the light receiving optical system 500 to focus on the light receiving sensor 7.

Note that a radius of rotation of the ring shaped pattern beam on a surface of the soft contact lens TL is convenient to measure if, for example, a diameter of the soft contact lens TL is 8.8 mm and a diameter of the ring shaped pattern beam is 2.5 mm, a diameter of rotation on the surface of the soft contact lens TL is set to become 3.5 mm as show in FIG. 11(b).

Figure 10:
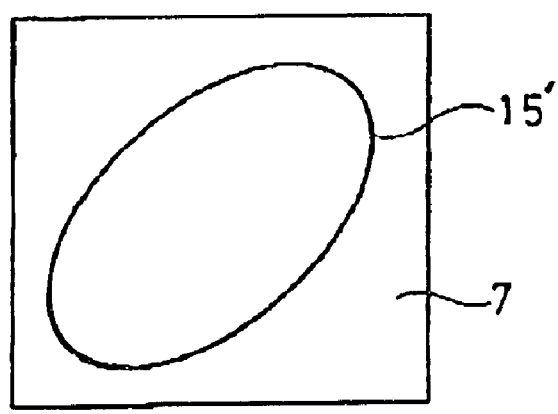
FIG. 10 is a view showing the elliptical shaped ring pattern projecting image.

The optical characteristic values S. C, A of the soft contact lens TL are obtained based on the ring shaped pattern projecting image 441" projected on the light receiving sensor 7. When astigmatism component is included in the soft contact lens TL, elliptical ring shaped pattern projecting image 15' is formed on the light receiving sensor 7 as shown in FIG. 10. If a large quantity of water is attached to the front and back surfaces 12a and 12b of the soft contact lens TL, the elliptical ring shaped pattern projecting image 15' formed on the light receiving sensor 7 is disarranged. The ring shaped pattern projecting image 15' is, also, disarranged if the front and back surfaces 12a and 12b of the soft contact lens TL are rough.

As a result, if the output of the light receiving sensor 7 is inputted in the SCA arithmetic circuit 13, the optical characteristic value data obtained by the SCA arithmetic circuit 13 are outputted to the residual quantity arithmetic circuit 14, the residual quantity if obtained similarly as the Embodiment 1, and whether the difference of the residual quantity if a predetermined value, the optical characteristic values S in air of the soft contact lens TL can be precisely measured similarly as the Embodiment 1.

According to the Embodiment 2, both of the refracting power of the examined eye E and the refracting power of the soft contact lens TL are measured. However, if the apparatus is constructed to use in only the measurement of the soft contact lens TL, the ring shaped pattern beam projecting optical system 400 and light receiving optical system 500 may be provided.

According to the configuration, even if the wet degree of the soft contact lens TL is not uniform, the optical characteristic values S, C, A can be measured with reducing the influence. Also, even if there is injury or dirt on the front and back surfaces of the soft contact lens TL and the soft contact lens TL is distorted, the optical characteristic values S, C, A can be measured with reducing the influence.

Note that it is preferable to provide the optical axis deflecting prism 490 in a position which is not conjugate with the back surface (a surface to contact with the cornea of the examined eye) of the soft contact lens TL in measuring the optical characteristic values of the soft contact lens TL.

Here, although a description has been made about the measurement of the soft contact lens, it is applicable the present invention to measure a hard contact lens or lenses of eyeglasses to have the similar advantageous effects. In this case, the residual quantity arithmetic circuit 14 is not required.

INDUSTRIAL APPLICABILITY

According to the present invention, because it is constructed as mentioned above, the optical characteristic values of the contact lens in air can be precisely measured.

What is claimed is:

1. A refracting power measuring apparatus comprising:
   a measuring optical system for projecting a measuring light toward a soft contact lens wet with liquid to measure optical characteristic values of the soft contact lens in air;
   a light receiving optical system having a light receiving sensor which receives the measuring light passed through the soft contact lens and outputs a received signal;
   an arithmetic circuit in which the received signal is inputted and computes the optical characteristic values based on the received signal;
   a residual quantity arithmetic circuit in which optical characteristic values data corresponding to the optical characteristic values of the arithmetic circuit are inputted every sample time and computes a residual quantity by means of a statistical processing based on the optical characteristic values data to output the residual quantity signal;
   a delay circuit for delaying the residual quantity signal a time corresponding to the sample time; and
   a comparing circuit for comparing the residual quantity signal delayed by the delay circuit with the following residual quantity signal and judging whether a difference between the delayed and following residual quantity signals is less than an allowed value,
   the optical characteristic values in air based on the judged results of the comparing circuit being obtained.

2. A refracting power measuring apparatus according to claim 1, wherein a setting switch is provided which establishes a measuring mode to measure the optical characteristic values of said soft contact lens in air.

3. A refracting power measuring apparatus according to claim 1, wherein said residual quantity is computed by receiving at least three beams or more as measuring beams.

4. A refracting power measuring apparatus according to claim 2, wherein said residual quantity is computed by receiving at least three beams or more as measuring beams.

5. A refracting power measuring apparatus according to claim 1, wherein said residual quantity is computed by receiving at least three beams or more as measuring beams, and a setting switch is provided which establishes a measuring mode to measure the optical characteristic values of said soft contact lens in air.

6. A refracting power measuring apparatus according to claim 1, wherein said measuring optical system is a pattern beam projecting optical system which projects a ring shaped pattern beam for measuring the refracting power of said soft contact lens on a reflected surface through said soft contact lens, said light receiving optical system guides the ring shaped pattern beam which is reflected on the reflected surface and returned through the soft contact lens to said light receiving element a portion of an optical system of the pattern beam projecting and light receiving optical systems is shared, provided an the shared portion of the pattern beam projecting and light receiving optical systems is a deflecting member which deflects and projects the ring shaped pattern beam with respect to an optical axis of the pattern beam projecting optical system.

7. A refracting power measuring apparatus according to claim 6, wherein said deflecting member is a deflecting prism which is rotated about the optical axis of said ring shaped pattern beam projecting optical system.

8. A refracting power measuring apparatus according to claim 6, wherein said reflected surface is disposed in a conjugate position with eye ground of a tested eye, the refracting power of the tested eye can be measured by use of the pattern beam projecting and light receiving optical systems in a state of removing said reflected surface.

9. A refracting power measuring apparatus according to claim 6, wherein said deflecting member is inserted into a position which is not conjugate with a disposed position of the soft contact lens in measuring the optical characteristic values of said soft contact lens.

10. A retracting power measuring apparatus according to claim 7, wherein said deflecting member is inserted into a position which is not conjugate with a disposed position of the soft contact lens in measuring the optical characteristic values of said soft contact lens.

11. A refracting power measuring apparatus according to claim 8, wherein said deflecting member is inserted into a position which is not conjugate with a disposed position of the soft contact lens in measuring the optical characteristic values of said soft contact lens.

12. A refracting power measuring apparatus comprising:
   a measuring optical system for projecting a measuring light toward a soft contact lens wet with liquid to measure optical characteristic values of the soft contact lens in air;

a light receiving optical system having a light receiving sensor which receives the measuring light passed through the soft contact lens and outputs a received signal;

an arithmetic circuit in which the received signal is input and computes the optical characteristic values based on the received signal;

a residual quantity arithmetic circuit in which optical characteristic values data corresponding to the optical characteristic values of the arithmetic circuit are input every sample time and computes a residual quantity by means of a statistical processing based on the optical characteristic values data to output the residual quantity signal;

a memory storing means to memorize the residual quantity computed by the residual quantity arithmetic circuit;

a judging means to judge whether a difference is a predetermined value with computing the difference in sequence of time based on the residual quantity stored in the memory storing means; and a display means to represent with extracting optical characteristic values corresponding to a difference which is less than a predetermined values.

13. A refracting power measuring apparatus according to claim 12, wherein said measuring optical system is a pattern beam projecting optical system which projects a ring shaped pattern beam for measuring the refracting power of said soft contact lens on a reflected surface through said soft contact lens, said light receiving optical system guides the ring shaped pattern beam which is reflected on the reflected surface and returned through the soft contact lens to said light receiving element, a portion of an optical system of the pattern beam projecting and light receiving optical systems is shared, provided in the shared portion of the pattern beam projecting and light receiving optical systems is a deflecting member which deflects and projects the ring shaped pattern beam with respect to an optical axis of the pattern beam projecting optical system.

14. A refracting power measuring apparatus according to claim 13, wherein said deflecting member is a deflecting prism which is rotated about the optical axis of said ring shaped pattern beam projecting optical system.

15. A refracting power measuring apparatus according to claim 13, wherein said reflected surface is disposed in a conjugate position with eye ground of a tested eye, the refracting power of the tested eye can be measured by use of the pattern beam projecting and light receiving optical systems in a state of removing said reflected surface.

16. A refracting power measuring apparatus according to claim 13, wherein said deflecting member is inserted into a position which is not conjugate with a disposed position of the soft contact lens in measuring the optical characteristic values of said soft contact lens.

17. A refracting power measuring apparatus according to claim 14, wherein said deflecting member is inserted into a position which is not conjugate with a disposed position of the soft contact lens in measuring the optical characteristic values of said soft contact lens.

18. A refracting power measuring apparatus according to claim 15, wherein said deflecting member is inserted into a position which is not conjugate with a disposed position of the soft contact lens in measuring the optical characteristic values of said soft contact lens.

* * * * *